United States Patent [19]

Wokalek et al.

[11] Patent Number: 4,905,700

[45] Date of Patent: Mar. 6, 1990

[54] METHOD OF TRANSMITTING ULTRASOUND INTO A BODY

[75] Inventors: Heinrich Wokalek; Wolfgang Strasser, both of Freiburg, Fed. Rep. of Germany

[73] Assignee: Ed. Geistlich AG fur Chemische Industrie, Lucerne, Switzerland

[21] Appl. No.: 154,525

[22] Filed: Feb. 5, 1988

Related U.S. Application Data

[63] Continuation of Ser. No. 870,349, Jun. 4, 1986, abandoned.

[30] Foreign Application Priority Data

Jun. 4, 1985 [GB] United Kingdom ............... 8514052

[51] Int. Cl.$^4$ .................. A61B 8/00; G01N 29/00
[52] U.S. Cl. .................. 128/660.01; 73/644; 128/915; 252/315.3; 524/55; 524/916
[58] Field of Search ............... 252/315.3; 128/660.01, 128/915; 73/644; 524/55, 916

[56] References Cited

U.S. PATENT DOCUMENTS

| | | | |
|---|---|---|---|
| 4,002,221 | 1/1977 | Buchalter | 128/660 X |
| 4,048,377 | 9/1977 | Boschetti et al. | 524/55 X |
| 4,383,529 | 5/1983 | Webster | 604/20 |
| 4,459,854 | 7/1984 | Richardson et al. | 73/644 |
| 4,702,732 | 10/1987 | Powers et al. | 128/803 X |

FOREIGN PATENT DOCUMENTS 0009430 4/1980 European Pat. Off. ......... 252/315.3

*Primary Examiner*—Richard D. Lovering
*Attorney, Agent, or Firm*—Bernard, Rothwell & Brown

[57] ABSTRACT

An acoustic coupling medium for transmitting ultrasound is disclosed. The medium, which is of use in ultrasonic visualization of the human body, comprises a sheet of hydrogel containing over 90% water, preferably over 95% water. The hydrogel preferably comprises agar, the chains of which are interspersed with chains of polyacrylamide.

5 Claims, No Drawings

METHOD OF TRANSMITTING ULTRASOUND INTO A BODY

This is a continuation of application Ser. No. 870,349, filed June 4, 1986, now abandoned.

This invention concerns improvements in or relating to coupling media for transmitting ultrasound, in particular for ultrasonic diagnosis.

Ultrasonic diagnosis represents an extremely safe and well-tolerated technique for investigation of the human body and, indeed, for investigation of other structures. It is of especial use in relation to young children or neonates where X-ray visualisation is inadvisable, particularly in screening programs. Other valuable areas of use include cerebral and cardiological visualisation and visualisation of superficial body structures such as the breast.

The available ultrasonic visualisation devices are, in use, directly applied to the area of the body to be studied and it is essential that the device makes virtually perfect contact with the appropriate body surface. Conventionally, ointment-like gels have been applied to the body surface as coupling media to ensure such contact. However, materials of this type must be used with care to ensure that there are no air bubbles between the acoustic device and the body surface. They may be impracticable or unsuitable for application in some cases, for example where the body surface is cut or abraded or body organs exposed during surgery are to be visualised and are frequently found to transmit sound inefficiently.

More recently, coupling media in the form of plastic bags containing thickened aqueous solutions have been proposed but these have been relatively expensive and have not always proved effective, in particular absorbing a large amount of sonic energy.

We have now found that hydrogels in sheet form provide extremely effective acoustic coupling media for transmitting ultrasound; especially good results are obtained if the gels contain over 90%, preferably over 95%, by weight of water, since their acoustic properties then approximate closely to those of the soft tissues of the body.

According to the present invention therefore we provide an acoustic coupling medium for transmitting ultrasound comprising a sheet of a hydrogel material containing over 90% by weight of water.

According to a further aspect of the invention we provide a process for the preparation of an acoustic coupling medium for transmission of ultrasound whereby a hydrogel containing over 90% by weight of water is prepared in sheet form.

Hydrogel sheets may readily be formed from hot aqueous solutions of gel-forming natural or synthetic polymers, for example polysaccharides such as agar, carrageenin, alginates and pectins (especially low methoxy pectins) and polypeptides and proteins such as gelatin. Alternatively, hydrogel sheets may be formed by polymerisation of water-soluble vinyl momomers in aqueous solution in the presence of a cross-linking agent such as a polyfunctional vinyl compound. Examples of such monomers include acrylic and methacrylic acid and their salts, amides and N-substituted amides, N-vinyl pyrrolidone and vinyl ethers of $C_{1-5}$ alkanols. Examples of cross-linking agents include ethylene glycol bis-acrylate, N,N'-methylene-bis-acrylamide, divinyl ether and diallyl maleate. It is also possible to produce hydrogel sheets by cross-linking water soluble polymers using cross-linking agents or ionising radiation followed by re-swelling with water; thus, for example, a film of polyvinyl alcohol may be cross-linked with ethylene diisocyanate while a sheet of high molecular weight polyethylene glycol may be cross-linked by irradiation with $Co^{60}$ gamma rays.

A still further possibility is to prepare cross-linked gelatin sheets by cross-linking aqueous gelatin with an aldehyde such as formaldehyde or glyoxal or by addition of a polyvalent metal salt such as aluminium sulphate.

Particularly good results have been obtained using hydrogels which contain a gel-forming protein, polypeptide or polysaccharide (such as one of those mentioned above) the chains of which are interspersed with chains of a hydrophilic synthetic polymer (such as one of the vinyl polymers mentioned above). Particularly useful gel-forming proteins and polysaccharides include gelatin and agar. The synthetic polymer is preferably an acrylic polymer having hydrophilic groupings, polyacrylamide being especially useful. The crosslinking agent is preferably an acrylate compound having at least two double bonds, for example N,N'-methylene-bis-acrylamide.

Such gels are capable of retaining large amounts of water while having excellent mechanical strength and good surface properties such as smoothness and lack of tackiness.

The hydrogel may conveniently contain 2 to 10% of the protein, polypeptide or polysaccharide and hydrophilic polymer together with the hydrophylic synthetic polymer, preferably containing 1 to 5% of the protein, polypeptide or polysaccharide and 1 to 5% of the synthetic polymer.

In order to ensure the sterility of the hydrogel, it may advantageously contain a disinfectant, conveniently an antibacterial compound such as taurolidine. The hydrogels thus may be kept in the fully hydrated state, for example in a water bath, for several months without microbial contamination.

The hydrogel is preferably used in the form of uniform, parallel-sided sheets. The thickness of the sheets is preferably in the range 3 to 25 mm e.g. 4 to 15 mm. In general, the sheets may be of a shape corresponding to the acoustic device, for example discs. The optimum thickness may depend on the position of the body structure to be visualised, that is the required focus of the ultrasonic device.

As indicated above, the hydrogels according to the invention exhibit excellent acoustic properties in transmitting sound in the frequencies commonly used in ultrasonic diagnosis, that is 5–10 MHz.

Thus, the sheet material of the invention may be used in conjunction with a scanning ultrasound diagnostic device with a 5 or 7.5 MHz transducer (a so-called B-scan device).

In the examination of superficial structures of the body, such as the thyroid gland or the breast, the hydrogel provides an efficient coupling medium which also, by spacing the head of the ultrasonic device from the structure in question, brings the latter into the optimal zone of examination of the device. There is excellent contact between the skin and the hydrogel and between the hydrogel and the ultrasonic device, with no air spaces or other voids which could affect acoustic transmission.

The hydrogel may be used advantageously in postoperative or intraoperative ultrasonic examinations as well as preoperative and screening examinations and may be directly applied not only to the skin but also to organs of the body exposed by surgery. As indicated, the use of the hydrogel as coupling medium may serve to bring the structure under examination into optimum focus.

The hydrogels here concerned may be prepared by forming the hydrophilic synthetic polymer in an aqueous solution containing the gel-forming protein, polypeptide or polysaccharide. Thus, a preferred hydrogel according to the invention may be prepared by dissolving acrylamide and an appropriate crosslinking agent such as N,N'-methylene-bis-acrylamide in an aqueous dispersion of agar and effecting polymerisation. When polymerisation is complete, any excess reagents can be removed by thorough washing, an antibacterial substance optionally being introduced at this stage. If desired, the gel may be partially dried for convenience in handling and storage and rehydrated prior to use.

The following Example is given by way of illustration only:

EXAMPLE 20g of agar-agar are suspended under agitation in 880g of deionized water and heated to 95° C. until complete dissolution. 1 l of a second aqueous solution containing 70g of acrylamide and 1.84 g of N,N'-methylene- bis-acrylamide is prepared at ambient temperature and added to the first solution with thorough mixing. Under continued agitation, 2.2 g of N,N,N',N'-tetrakis(2-hydroxypropyl)-ethylene diamine dissolved in 60 g of water and then 1.26 g of ammonium peroxidisulfate dissolved in 40 g of water are added. The solution is poured into moulds to provide, after polymerization, 100 mm×200 mm sheets of thickness 10 mm containing over 95% by weight of water.

The mixture has a temperature between 50° C. and 55° C. and begins to polymerize immediately. After 10 minutes the gel point is reached. The batch is allowed to cool down overnight during which time polymerization is completed.

The gel is freed from soluble impurities by washing in pure flowing water for 24 hours.

Sheets of acoustic coupling medium as prepared above have been used in dermatological sonographic studies, including diagnosis of lymph node metastases, congenital nevis, malignant melamona and granuloma pyogenicum, using a B-scan ultrasonic device.

We claim:

1. A method of transmitting ultrasound into a body which comprises passing ultrasound from a transmitter into said body through an acoustic coupling medium which is in contact with the transmitter but which is separate therefrom, the acoustic coupling medium comprising a sheet of hydrogel material containing over 95% by weight of water, in which the hydrogel contains agar, the chains of which are interspersed with chains of polyacrylamide.

2. A method in which the hydrogel is in the form of uniform, parallel-sided sheets the thickness of which is in the range 3 to 25 mm.

3. A method of transmitting ultrasound into a body which comprises the steps of:
   (a) applying a sheet of hydrogel material containing over 95% by weight of water to a body, wherein the hydrogel contains agar, the chains of which are interspersed with the chains of polyacrylamide;
   (b) contacting the sheet of hydrogel material with an ultrasound transmitter; and
   (c) passing ultrasound from said transmitter into said body through said sheet of hydrogel material.

4. A method as claimed in claim 3, wherein the ultrasound is transmitted into a human body for diagnostic purposes.

5. The method of claim 3 wherein the hydrogel is in the form of a uniform, parallel-sided sheet, the thickness of which is in the range of 3–25 mm.

* * * * *

UNITED STATES PATENT AND TRADEMARK OFFICE
CERTIFICATE OF CORRECTION

PATENT NO. : 4,905,700

DATED : March 6, 1990

INVENTOR(S) : Heinrich WOKALEK et al.

It is certified that error appears in the above-identified patent and that said Letters Patent is hereby corrected as shown below:

Col. 1, line 60, "momomers" should be --monomers--.

Col. 4, line 21, after "method" insert --as claimed in claim 1,--.

Signed and Sealed this

Twenty-second Day of October, 1991

Attest:

HARRY F. MANBECK, JR.

Attesting Officer

Commissioner of Patents and Trademarks